United States Patent
Sugiyama et al.

(10) Patent No.: US 9,393,554 B2
(45) Date of Patent: Jul. 19, 2016

(54) METHOD FOR PRODUCING SATURATED ALDEHYDE FROM 1,2-ALKANEDIOL

(71) Applicants: TOKUSHIMA UNIVERSITY, Tokushima-shi (JP); MITSUBISHI RAYON CO., LTD., Chiyoda-ku (JP)

(72) Inventors: Shigeru Sugiyama, Tokushima (JP); Yuuki Katou, Otake (JP); Toshiya Yasukawa, Otake (JP); Shuji Akihara, Otake (JP); Wataru Ninomiya, Otake (JP)

(73) Assignees: TOKUSHIMA UNIVERSITY, Tokushima-shi (JP); MITSUBISHI RAYON CO., LTD., Chiyoda-ku (JP)

(*) Notice: Subject to any disclaimer, the term of this patent is extended or adjusted under 35 U.S.C. 154(b) by 0 days.

(21) Appl. No.: 14/654,996

(22) PCT Filed: Feb. 4, 2014

(86) PCT No.: PCT/JP2014/052485
§ 371 (c)(1),
(2) Date: Jun. 23, 2015

(87) PCT Pub. No.: WO2014/123095
PCT Pub. Date: Aug. 14, 2014

(65) Prior Publication Data
US 2015/0343429 A1 Dec. 3, 2015

(30) Foreign Application Priority Data
Feb. 6, 2013 (JP) .................. 2013-021299

(51) Int. Cl.
*C07C 45/51* (2006.01)
*B01J 29/03* (2006.01)
*B01J 35/10* (2006.01)
*B01J 29/035* (2006.01)
*C07C 45/52* (2006.01)
*C07C 47/02* (2006.01)

(52) U.S. Cl.
CPC ............ *B01J 29/0308* (2013.01); *B01J 29/035* (2013.01); *B01J 35/1061* (2013.01); *C07C 45/52* (2013.01); *C07C 47/02* (2013.01)

(58) Field of Classification Search
CPC .................. C07C 45/52; B01J 29/03

USPC .......................................... 568/486
See application file for complete search history.

(56) References Cited

FOREIGN PATENT DOCUMENTS

| CN | 101733145 | 6/2010 |
|----|-----------|--------|
| JP | 7 116083 | 5/1995 |
| JP | 2662965 | 10/1997 |
| JP | 11 35510 | 2/1999 |
| JP | 2010 180156 | 8/2010 |
| JP | 2010 227925 | 10/2010 |

OTHER PUBLICATIONS

Inagaki et al. Synthesis of Highly Ordered Mesoporous Materials from a Layered Polysilicate. Journal of the Chemical Society Communications, 1993, p. 680-682.*
Weissermel, K., et al., Industrial Organic Chemistry, Fourth Edition, (2003), (pp. 165-166).
Weissermel, K., et al., Industrial Organic Chemistry, Fourth Edition, (2003), (pp. 131-134).
Mori, K., et al., "Catalytic dehydration of 1,2-propanediol into propanal", Applied Catalysis A: General, vol. 366, (2009), (pp. 304-308).
Zhang, D., et al., "Dehydration of 1,2-propanediol to propionaldehyde over zeolite catalysts", Applied Catalysis A: General, vol. 400, (2011), (pp. 148-155).
Okada, Y., et al., "FSM-16 ni yoru 1,2-Propanediol kara Propionaldehyde no Gosei", Abstracts of Annual Meeting of the Society of Chemical Engineers, (Feb. 17, 2013), vol. 78, (Total pp. 2).
International Search Report Issued Mar. 18, 2014 in PCT/JP2014/052485 Filed Feb. 4, 2014.
Chinese Office Action issued Mar. 11, 2016, in corresponding Chinese Patent Application No. 201480007398.X (with English-language Translation).
Sugiyama Shigeru et al., "The Catalytic Conversion of 1,2-Propandiol to Propanal on FSM-16 Molded by Wet-Treatment and Pressurization," *Journal of Chemical Engineering of Japan*, vol. 46, $9^{th}$ Period, pp. 620-624 Sep. 20, 2013.
Zhang Yan Xia, "Study on the Synthesis and Apply of Mesoporous Molecular Sieves FSM-16," *Chinese Excellent Master Degree Paper full-text database, Science Technology*, Course 1, $7^{th}$ Period, pp. B014-153 Jul. 5, 2010.

* cited by examiner

*Primary Examiner* — Sikarl Witherspoon
(74) *Attorney, Agent, or Firm* — Oblon, McClelland, Maier & Neustadt, L.L.P

(57) ABSTRACT

Provided is a method that produces a saturated aldehyde from a 1,2-alkanediol in high yield. Disclosed is a method for producing a saturated aldehyde from a 1,2-alkanediol in the presence of a regular mesoporous material.

15 Claims, No Drawings

METHOD FOR PRODUCING SATURATED ALDEHYDE FROM 1,2-ALKANEDIOL

TECHNICAL FIELD

The present invention relates to a method for producing a saturated aldehyde from a 1,2-alkanediol. In particular, the invention relates to a method for producing a saturated aldehyde by bringing a 1,2-alkanediol into contact with a regular mesoporous material synthesized by the reaction of a layered silicate with a surfactant.

BACKGROUND ART

Saturated aldehydes represented by propionaldehyde are an important substance in the chemical industry to be used as a starting material of solvents, an intermediate of chemical products, a solvent for pharmaceutical intermediate production and the like. The production methods of lower saturated aldehydes are significantly different depending on the number of carbon atoms constituting the aldehydes. For example, acetaldehyde of a C2 aldehyde is industrially produced by the Wacker oxidation of ethylene (Non-Patent Document 1). In addition, it is general to produce butyraldehyde of a C4 aldehyde by the hydroformylation reaction of propylene (Non-Patent Document 2).

Meanwhile, propionaldehyde of a C3 aldehyde can be obtained by the hydroformylation reaction of ethylene (Non-Patent Document 2). In addition, propionaldehyde can be obtained by the partial hydrogenation of allyl alcohol as a starting material which is obtained through the hydrolysis of allyl acetate obtained by the acetoxylation of propylene (Patent Document 1) or through the isomerization of propylene oxide as a starting material (Patent Document 2).

However, extensive capital investment is required for the construction of the hydroformylation reaction equipment. In addition, the acetoxylation of propylene requires a corrosion resistant facility since acetic acid is used in the reaction, and thus extensive capital investment is required as well. On the other hand, propylene oxide is difficult to handle due to its high reactivity in the case of using propylene oxide as the starting material. Furthermore, in the case of obtaining a saturated aldehyde by the partial hydrogenation of allyl alcohol as the starting material, there is a case in which a part of the carbonyl moiety is also hydrogenated to decrease the selectivity of the target product. Moreover, a method to obtain propionaldehyde by the dehydrogenation of 1-propanol is also known, but there is a problem in the supply of 1-propanol of the starting material. In addition, a method is reported (Patent Document 3) in which propionaldehyde of a lower saturated aldehyde is synthesized using 1,2-propanediol as the starting material and a heteropoly acid or a heteropoly acid-catalyst support composite as a catalyst.

CITATION LIST

Patent Document

Patent Document 1: JP 2662965 B1
Patent Document 2: JP 7-116083 B
Patent Document 3: JP 2010-180156 A

Non-Patent Document

Non-Patent Document 1: Industrial Organic Chemistry, Wiley, 4th edition p. 165

Non-Patent Document 2: Industrial Organic Chemistry, Wiley, 4th edition p. 131

SUMMARY OF THE INVENTION

Problem to be Solved by the Invention

However, the selectivity of the saturated aldehyde is low although the catalytic activity is high in a predetermined condition in the prior production method to produce a saturated aldehyde using a 1,2-alkanediol as the starting material, and thus the development of a method that can produce a saturated aldehyde in higher yield is strongly desired when considering the industrial use. An object of the invention is to provide a method that can produce a saturated aldehyde from a 1,2-alkanediol in high yield.

Means for Solving Problem

The invention has been made as a result of intensive investigations of the present inventors to achieve the above object.

The method according to the invention produces a saturated aldehyde from a 1,2-alkanediol in the presence of a regular mesoporous material.

Effect of the Invention

According to the invention, it is possible to produce a saturated aldehyde from a 1,2-alkanediol in high yield.

MODE(S) FOR CARRYING OUT THE INVENTION

In the method according to the invention, a saturated aldehyde is produced from a 1,2-alkanediol in the presence of a regular mesoporous material. In the invention, the use of a regular mesoporous material as the catalyst makes it possible to produce a saturated aldehyde from a 1,2-alkanediol in high yield.

[Regular Mesoporous Material]

The regular mesoporous material in the invention refers to a silica-based material which has regularly arranged pores with a diameter of from 2 to 50 nm. It is possible to confirm that a material is a regular mesoporous material by obtaining an X-ray diffraction peak using a powder X-ray diffractometer (product name: Rigaku RINT 2500 VHF, Rigaku Corporation). It is possible to use a solid acid catalyst having a high acid strength as the regular mesoporous material according to the invention. In general, silica, alumina and the like are used as the solid acid catalyst, but the use of the regular mesoporous material as in the invention makes it possible to produce a saturated aldehyde from a 1,2-alkanediol in high yield since the hydroxyl group present inside the regularly arranged mesopores has high performance as an acid catalyst in addition to an increase in the reaction area due to a high specific surface area.

A regular mesoporous material which is synthesized by the reaction of a layered silicate with a surfactant is preferable as the regular mesoporous material. Examples thereof may include a regular mesoporous material synthesized by the method described in S. Inagaki et al., J. Chem. Soc., Chem. Commun., No. 8, 680-682 (1993). The regular mesoporous material which is synthesized by the reaction of a layered silicate with a surfactant has a structure in which the periodically curved silicate sheets are vertically coupled at the convex portions and countless numbers of uniformly aligned pores are present in the gap between the sheets. The pores have a diameter of from 2 to 10 nm and are distributed around a certain diameter in a narrow range. It is possible to change the diameter of pores by the length of the alkyl chain length in the case of using, for example, an alkyltrimethylammonium as the surfactant. Among them, it is preferable to produce FSM-16 as the regular mesoporous material using hexadecyltrimethylammonium ($C_{16}H_{33}N(CH_3)_3$).

It is possible to use kanemite ($NaHSi_2O_5 \cdot 3H_2O$), sodium disilicate crystals (α, β, γ, σ-$Na_2Si_2O_5$), makatite ($Na_2Si_4O_9 \cdot 5H_2O$), ilerite ($Na_2Si_8O_{17} \cdot xH_2O$), magadiite ($Na_2Si_{14}O_{29} \cdot xH_2O$), kenyaite ($Na_2Si_{20}O_{41} \cdot xH_2O$) and the like as the layered silicate used in the synthesis of the regular mesoporous material. Among these, kanemite is preferable as the layered silicate. One kind or two or more kinds of these layered silicates may be used.

It is possible to use a chloride, a bromide, an iodide or a hydroxide of an alkyltrimethylammonium, a dimethyldialkylammonium, an alkylammonium and a benzylammonium, and the like as the surfactant used in the synthesis of the regular mesoporous material. Among these, a bromide of an alkyltrimethylammonium is preferable as the surfactant. A linear or branched alkyl group having from 8 to 18 carbon atoms is preferable as the alkyl group of a chloride, a bromide, an iodide or a hydroxide of an alkyltrimethylammonium, a dimethyldialkylammonium and an alkylammonium. One kind or two or more kinds of these surfactants may be used.

Examples of the method to synthesize the regular mesoporous material by the reaction of a layered silicate with a surfactant may include a method in which the layered silicate described above is dispersed in a solvent prepared by dissolving a surfactant. The solvent is preferably water but may be a water-alcohol mixed solvent or another solvent. The concentration of the surfactant is preferably from 0.05 to 1 mol/L. With regard to the dispersed amount of the layered silicate, for example, 5 to 200 g of kanemite with respect to 1000 ml of a 0.1 mol/L aqueous solution of a surfactant is preferable. The reaction temperature is preferably from 50 to 150° C. It is preferable to stir the dispersion solution during heating. The pH of the dispersion solution is preferably 10 or more for from 1 to 5 hours at the beginning and 10 or less for the rest of the time. Kanemite is alkaline, and thus the pH of the dispersion solution is 10 or more even without any treatment. It is possible to adjust the pH to 10 or more by adding sodium hydroxide in a case in which the pH is 10 or less. Thereafter, the pH of the solution can be lowered to 10 or less by adding an acid such as hydrochloric acid. It is preferable to lower the pH of the solution to 8.5. It is possible to obtain a regular mesoporous material which exhibits particularly high crystallinity and heat resistance by the pH control. Thereafter, the solid product is recovered by filtration. The reaction time is preferably from 1 to 20 hours. Meanwhile, the reaction time refers to the time from when the layered silicate and the surfactant are mixed together until when the solid product is filtered. It is possible to obtain a regular mesoporous material exhibiting high heat resistance by repeatedly washing the solid product with deionized water and the like. It is possible to remove the surfactant incorporated in the crystal by calcining the solid product at a temperature of 550° C. or higher or treating with a hydrochloric acid/ethanol mixed solution after drying the solid product, thereby to obtain a regular mesoporous material. As the calcining condition in the case of performing calcination, it is preferable to heat the solid product for 1 hour or longer under an atmosphere of air, oxygen, nitrogen or the like. In addition, in the case of treating with a hydrochloric acid/ethanol mixed solution, other acids and other organic solvents other than hydrochloric acid and ethanol may be used as long as a combination of an acid/an organic solvent.

The regular mesoporous material thus obtained is a regular mesoporous material having a periodic structure. Meanwhile, it is possible to confirm that the regular mesoporous material is a regular mesoporous material having a periodic structure by the presence of one or more X-ray diffraction peaks including the maximum peak at the d value of 2 nm or more in the structural analysis by X-ray.

Examples of the regular mesoporous material other than the regular mesoporous material obtained by the reaction of a layered silicate with a surfactant may include MCM-41, MCM-48, SBA-15, SBA-16, HMS, KIT-16 and KIT-5. One kind or two or more kinds of these may be used. These regular mesoporous materials can be produced by known methods.

In the case of using in the invention, the lower limit of the average pore size of the regular mesoporous material (hereinafter, referred to as pore size) is preferably 2.0 nm or more, more preferably 2.3 nm, and even more preferably 2.5 nm or more. The upper limit of the pore size is preferably 10.0 nm or less, more preferably 5.0 nm or less, and even more preferably 3.5 nm or less. It is believed that the regular mesoporous material exhibits a unique acid strength since the hydroxyl groups present on the wall surface of the mesopores are positioned towards the center of the pores from the wall surface and the hydroxyl groups are present in a high density in the pore center.

It is preferable that the pore size be 2.0 nm or more since the reactant be easily incorporated into the space of the hydroxyl groups arranged towards the center. In addition, it is preferable that the pore size be 10.0 nm or less since it is within the range in which the contact of hydroxyl group with the reactant sufficiently occurs and the space of the hydroxyl group is large enough to easily incorporate the reactant thereinto.

The lower limit of the acid quantity of the regular mesoporous material is preferably 1.0 mmol/g or more, more preferably 1.5 mmol/g or more, and even more preferably 2.0 mmol/g or more. The upper limit of the acid quantity is preferably 10.0 mmol/g or less, more preferably 6.0 mmol/g or less, and even more preferably 4.0 mmol/g or less. The acid quantity means the quantity of hydroxyl group. It is preferable that the acid quantity be 1.0 mmol/g or more since it is the minimum quantity required for the hydroxyl group present on the wall surface of the mesopores to be in a high density state. In addition, it is preferable that the acid quantity be 10.0 mmol/g or less since the hydroxyl groups exist more than required and thus the product also reacts as the acid quantity increases to be the cause of a decrease in selectivity in some cases.

The measurement of acid quantity of the regular mesoporous material is performed using an amine titration method and is calculated from the titer of butylamine. The acid quantity of the regular mesoporous material is calculated from the sum of the titer of butylamine at the time of adding each indicator, and four kinds of indicators of methyl red, 4-phenylazo-1-naphthylamine, p-dimethylaminoazobenzene and 4-phenylazodiphenylamine are used as the indicator.

[Method for Producing Saturated Aldehyde from 1,2-Alkanediol]

Specific examples of the 1,2-alkanediol as the starting material in the method according to the invention may include 1,2-propanediol, 1,2-butanediol, 1,2-pentanediol and 1,2-hexanediol. Among these, 1,2-propanediol is preferable as the 1,2-alkanediol from the viewpoint that 1,2-propanediol can be produced from glycerin of a by-product obtained when producing the biodiesel fuel.

In addition, examples of the saturated aldehyde produced by the method according to the invention may include formaldehyde, acetaldehyde, propionaldehyde, butyraldehyde, pentyl aldehyde, hexyl aldehyde and the like. Among these, propionaldehyde is preferable as the saturated aldehyde since propionaldehyde is also used in the starting material of an acrylic monomer such as methyl propionate.

The method according to the invention can be carried out, for example, by the gas phase flow type in which a 1,2-alkanediol of the starting material is gasified so as to pass through the catalyst layer containing a regular mesoporous material. In this case, an inert gas such as helium or nitrogen may be allowed to coexist in the gas of the starting material to be used. In addition, water may be contained in the starting material.

The temperature of the catalyst layer, that is, the temperature of the regular mesoporous material is preferably from 200 to 800° C., more preferably from 300 to 600° C., and even more preferably from 350 to 500° C. when it is carried out by the method described above. High catalytic activity is obtained when the temperature of the regular mesoporous material is 200° C. or higher. In addition, it is possible to suppress a decrease in selectivity of the desired product and a decrease in catalytic activity due to the thermal decomposition of the starting material when the temperature of the regular mesoporous material is 800° C. or lower.

The reaction pressure can be appropriately selected depending on the kind of the 1,2-alkanediol used in the reaction and is usually 1 MPa or less and preferably the atmospheric pressure. The reaction can be conducted by a fixed bed flow reaction method in which a gas mixture containing a 1,2-alkanediol of the starting material, an inert gas and the like passes through a reactor filled with a catalyst.

The W/F is preferably from 0.001 to 1000 g·min/ml, more preferably from 0.01 to 100 g·min/ml, and even more preferably from 1 to 40 g·min/ml. It is preferable that the W/F be 0.001 g·min/ml or more since a high conversion rate can be maintained. In addition, it is preferable that the W/F be 1000 g·min/ml or less since the product also reacts when the reactivity is too high and thus a decrease in selectivity and the deterioration of catalyst are caused in some cases. Meanwhile, W is the mass (g) of catalyst filled in the reaction tube and F is the supply rate (ml/min) of 1,2-alkanediol to be supplied to the layer filled with a catalyst. In other words, the W/F is the mass of catalyst filled in the reaction tube with respect to the supply rate of 1,2-alkanediol to be supplied thereto and is calculated by the following Equation.

$W/F$=quantity (g) of catalyst to be filled/supply rate (ml/min) of 1,2-alkanediol to be supplied to reaction tube

EXAMPLES

Hereinafter, the invention will be described in more detail with reference to Examples and Comparative Examples, but the invention is not limited to these Examples.

The periodic structure of the regular mesoporous material was confirmed by obtaining the X-ray diffraction peak using a powder X-ray diffractometer (product name: Rigaku RINT 2500 VHF, Rigaku Corporation).

The pore size of the regular mesoporous material is calculated from the position of the peak of the pore size distribution curve created as follows. The pore size distribution curve refers to a curve created by plotting the value (dV/dD) obtained by differentiating the pore volume (V) by the pore diameter (D) with respect to the pore diameter (D). The pore distribution curve was determined by a calculation method of the BJH method after obtaining the nitrogen adsorption isotherm using a gas adsorption apparatus (product name: BEL-SORP-max, BEL Japan, Inc.).

In the production method of saturated aldehyde, the analysis of the mixed gas of the starting material and the product was performed using gas chromatography. The conversion rate of 1,2-alkanediol, the selectivity of saturated aldehyde and the yield of saturated aldehyde were determined from the results of gas chromatography by the following Equations.

Conversion rate of 1,2-alkanediol (%)=$(B/A) \times 100$

Selectivity of saturated aldehyde (%)=$(C/B) \times 100$

Yield of saturated aldehyde (%)=$(C/A) \times 100$

In Equations, A is the number of moles of the supplied 1,2-alkanediol, B is the number of moles of the reacted saturated aldehyde, C is the number of moles of the produced saturated aldehyde.

Example 1

For 6 hours, 5.0 g of sodium silicate was calcined at 700° C. The sodium silicate thus calcined was added into 50 mL of distilled water, stirred for 3 hours at room temperature, and filtered, thereby to obtain a paste of kanemite which is a layered silicate. To the kanemite paste thus obtained, 100 ml of 0.1 mol/L aqueous solution of hexadecyltrimethylammonium bromide was added, and the mixture was stirred and maintained for 3 hours at 70° C. Thereafter, the pH thereof was adjusted to 8.5 using a 2 mol/L aqueous solution of hydrochloric acid and subsequently stirred and maintained for 18 hours at 70° C. Thereafter, the resultant was filtered, washed with distilled water several times, and dried, thereby to obtain a precursor of regular mesoporous material FSM-16. The precursor was then calcined for 8 hours at 550° C. in an air atmosphere, thereby to obtain a regular mesoporous material FSM-16.

The result of the structural analysis by X-ray confirmed that the regular mesoporous material thus obtained was a regular mesoporous material having a diffraction peak of the d value at the position of 4.0 nm or more and a periodic structure.

The regular mesoporous material thus obtained was packed into the quartz reaction tube that is installed in a fixed bed flow type reactor and has a diameter of 9 mm and a length of 35 mm. The reaction tube was kept at 400° C. by an electric furnace. Next, oxygen gas was allowed to pass through inside the reaction tube for 1 hour at a flow rate of 30 ml/min under the atmospheric pressure. Thereafter, nitrogen was allowed to pass through at a flow rate of 30 ml/min, 1,2-propanediol was gasified at a flow rate of 0.028 ml/min and supplied to the packed layer of regular mesoporous material together with nitrogen, and the reaction to convert 1,2-propanediol into propionaldehyde was conducted. Meanwhile, the respective conditions were set so as to have a W/F of 10.7 g·min/ml.

The reaction tube outlet gas was measured after 15 minutes from the start of the reaction by gas chromatography, and the conversion rate of 1,2-propanediol, the selectivity of propionaldehyde and the yield of propionaldehyde were determined. The results are presented in Table 1.

Example 2

The production of propionaldehyde was performed in the same manner as in Example 1 except that the respective conditions were set so as to have a W/F of 21.4 g·min/ml and the reaction tube outlet gas was measured after 105 minutes from the start of the reaction. The results are presented in Table 1.

Example 3

Into 96.2 mL of distilled water, 33.8 g of dodecyltrimethylammonium bromide was added so as to obtain solution A.

In addition, 1.7 g of sodium hydroxide was dissolved in 18.8 mL of distilled water so as to obtain solution B. While stirring the solution A, the solution B and silica sol (trade name: SNOWTEX 20 manufactured by NISSAN CHEMICAL INDUSTRIES, LTD.) were alternately added thereto little by little. The resultant was stirred for 2 hours at room temperature after adding the entire amount, thereby to obtain a mixture.

The mixture thus obtained was subjected to the hydrothermal treatment for 48 hours at 140° C. in the autoclave. The resulting white solid was filtered, washed, and dried for 24 hours at 60° C.

The white solid thus obtained was dispersed in distilled water. At this time, the mass of distilled water used was 30 times larger than that of the white solid. Thereafter, 2 mol/L of hydrochloric acid was gradually added thereto so as to have a pH of 6.5. The resultant was kept at 80° C. when the pH was stabilized and allowed to stand for 20 hours. Thereafter, the resultant was filtered, washed and dried for 24 hours at 60° C., thereby to obtain MCM-41. The production of propionaldehyde was performed in the same manner as in Example 2 except that MCM-41 thus obtained was packed into the reaction tube of the fixed bed flow type reactor. The results are presented in Table 1.

Comparative Example 1

The production of propionaldehyde was performed in the same manner as in Example 2 except that $SiO_2$ (trade name: CAB-O-SIL manufactured by Cabot Corporation) was packed into the reaction tube of the fixed bed flow type reactor. The results are presented in Table 1. Meanwhile, the CAB-O-SIL does not have regularly arranged mesopores and thus does not correspond to a regular mesoporous material.

Comparative Example 2

The aqueous solution prepared by dissolving 0.5 g of tungstosilicic acid in 5 g of distilled water was added to $SiO_2$, distilled water that was the solvent was then distilled off therefrom under reduced pressure using an evaporator, thereby to obtain $SiW_{12}O_{40}/SiO_2$. The production of propionaldehyde was performed in the same manner as in Example 2 except that $SiW_{12}O_{40}/SiO_2$ thus obtained was packed into the reaction tube of the fixed bed flow type reactor. The results are presented in Table 1. Meanwhile, $SiW_{12}O_{40}/SiO_2$ thus obtained does not have regularly arranged mesopores and thus does not correspond to a regular mesoporous material.

TABLE 1

| | W/F (g·min/ml) | Pore size (nm) | Acid quantity (mmol/g) | Conversion rate (%) | Selectivity (%) | Yield (%) |
|---|---|---|---|---|---|---|
| Example 1 | 10.7 | 2.7 | 2.7 | 67.5 | 93.4 | 63.0 |
| Example 2 | 21.4 | 2.7 | 2.7 | 96.1 | 55.2 | 53.0 |
| Example 3 | 21.4 | 3.2 | 2.5 | 97.7 | 43.6 | 42.5 |
| Comparative Example 1 | 21.4 | — | 0.7 | 3.4 | 32.1 | 1.1 |
| Comparative Example 2 | 21.4 | — | — | 14.4 | 56.2 | 8.0 |

As described above, it is possible to efficiently produce a saturated aldehyde by synthesizing the saturated aldehyde from a 1,2-alkanediol using a regular mesoporous material. It is possible to more efficiently produce a saturated aldehyde when a regular mesoporous material which is synthesized by the reaction of a layered silicate with a surfactant is used.

This application is based upon and claims the benefit of priority of the prior Japanese Patent Application No. 2013-21299, filed on Feb. 6, 2013, the entire contents of which are incorporated herein by reference.

The present invention has been described with reference to embodiments and Examples, but the invention is not intended to be limited to the above embodiments and Examples. It should be understood by those skilled in the art that various modifications may be included in the configuration and details of the invention as they are within the scope of the invention.

The invention claimed is:

1. A method for producing a saturated aldehyde, the method comprising contacting a 1,2-alkanediol with a regular mesoporous material to convert the 1,2-alkanediol into a saturated aldehyde, wherein the regular mesoporous material is a regular mesoporous material obtained by reacting a layered silicate with a surfactant.

2. The method according to claim 1, wherein an average pore size of the regular mesoporous material is 2.0 nm or more and 10.0 nm or less.

3. The method according to claim 1, wherein an acid quantity of the regular mesoporous material is 1.0 mmol/g or more and 10.0 mmol/g or less.

4. The method according to claim 1, wherein the layered silicate is selected from kanemite ($NaHSi_2O_5 \cdot 3H_2O$), sodium disilicate crystals (α, β, γ, σ-$Na_2Si_2O_5$), makatite ($Na_2Si_4O_9 \cdot 5H_2O$), ilerite ($Na_2Si_8O_{17} \cdot xH_2O$), magadiite ($Na_2Si_{14}O_{29} \cdot xH_2O$), and kenyaite ($Na_2Si_{20}O_{41} \cdot xH_2O$).

5. The method according to claim 1, wherein the regular mesoporous material is FSM-16.

6. The method according to claim 1, wherein the 1,2-alkanediol is 1,2-propanediol.

7. The method according to claim 1, wherein the saturated aldehyde is propionaldehyde.

8. The method according to claim 1, wherein the 1,2-alkanediol is contacted with a regular mesoporous material such that W/F is 0.01 g·min/ml or more and 1000 g·min/ml or less.

9. The method according to claim 1, wherein a temperature of the regular mesoporous material during the contacting is set to 200° C. or higher and 800° C. or lower.

10. The method according to claim 1, wherein
the 1,2-alkanediol is 1,2-propanediol,
the saturated aldehyde is propionaldehyde,
the 1,2-propanediol is contacted with the regular mesoporous material such that W/F is 0.01 g·min/ml or more and 1000 g·min/ml or less, a temperature of the regular mesoporous material during the contacting is set to 200° C. or higher and 800° C. or lower, and the yield of propionaldehyde is at least 42.5%.

11. The method according to claim 10, wherein the regular mesoporous material is FSM-16.

12. The method according to claim 10, wherein the regular mesoporous material is MCM-41.

13. The method according to claim 1, wherein the yield of saturated aldehyde is at least 42.5%.

14. The method according to claim 1, wherein the yield of saturated aldehyde is at least 42.5%-63.0%.

15. The method according to claim 10, wherein the yield of propionaldehyde is 42.5%-63.0%.

* * * * *